United States Patent [19]
Brotz

[11] Patent Number: 5,092,679
[45] Date of Patent: Mar. 3, 1992

[54] MELTING POINT DETERMINATION APPARATUS AND METHOD

[76] Inventor: Gregory R. Brotz, P.O. Box 1322, Sheboygan, Wis. 53081

[21] Appl. No.: 627,310

[22] Filed: Dec. 14, 1990

[51] Int. Cl.⁵ .................................................. G01N 25/04
[52] U.S. Cl. ........................................ 374/19; 374/17; 374/24
[58] Field of Search ................ 374/16, 17, 18, 19, 374/20, 24; 250/215, 238

[56] References Cited

U.S. PATENT DOCUMENTS

| | | | |
|---|---|---|---|
| 2,658,382 | 11/1953 | VanderKamp | 374/17 |
| 2,669,863 | 2/1954 | Shapiro | 374/17 |
| 2,697,933 | 12/1954 | Donath | 374/18 |
| 3,077,764 | 2/1963 | Kopff | 374/19 |
| 3,161,039 | 12/1964 | Kapff | 374/20 |
| 4,377,001 | 3/1983 | Takeda et al. | 374/17 |
| 4,484,822 | 11/1984 | Hancock | 374/16 X |
| 4,601,587 | 7/1986 | Mathiprakasam | 374/16 X |
| 4,908,835 | 3/1990 | Nishiuchi et al. | 374/17 X |

FOREIGN PATENT DOCUMENTS

| | | | |
|---|---|---|---|
| 2708365 | 8/1978 | Fed. Rep. of Germany | 374/17 |
| 3247689 | 6/1984 | Fed. Rep. of Germany | 374/18 |
| 244349 | 9/1989 | Japan | 374/16 |
| 851221 | 7/1981 | U.S.S.R. | 374/16 |
| 2202941 | 10/1988 | United Kingdom | 374/16 |

Primary Examiner—William A. Cuchlinski, Jr.
Assistant Examiner—G. Bradley Bennett
Attorney, Agent, or Firm—William Nitkin

[57] ABSTRACT

A device and method for determining the melting point of a material having light reflective properties by determining changes in the reflective properties of the material while under pressure as it is being heated.

5 Claims, 5 Drawing Sheets

MELTING POINT DETERMINATION APPARATUS AND METHOD

BACKGROUND OF THE INVENTION

1. Field of the Invention

This invention resides in the area of apparatuses and methods used for the determination of melting points of materials and more particularly relates to an apparatus and method which determine the melting point of a material by changes in reflective properties of the material under different temperatures and pressures.

2. Description of the Prior Art

Many methods are used to determine melting points for materials. The simplest are types where observers note temperatures at which materials, upon heating, become transparent. Such methods first involve immersing the particle of material whose melting point is to be determined in a non-solvent which is heated at a known rate. As the heat from the medium is transferred into the particle, at the point where the temperature of the medium is equal to the melting point of the particle, the particle changes its optical transmissivity and also may change its physical shape. Another method of measuring the melting point of a material utilizes scanning calorimetry techniques or temperature gradient bars where a physical determination of the melting point at which a material will stick to a heat bar is made.

A problem with many of the prior art melting point determination apparatuses is that they lack absolute accuracy in that they require the judgment of an observer as to when a reaction has taken place, and this judgment can vary from observer to observer. Further, many materials can be amorphous in nature and exhibit a range of melting points which many prior art devices do not detect. It has been appreciated in the prior art regarding melting point apparatuses that a substance may change its light transmissibility at its melting point and apparatuses to measure the change in light transmission when a material passes from a solid continuous phase to a liquid continuous phase is disclosed in U.S. Pat. No. 2,669,863 by Shapiro. Further the use of different pressures when determining melting point is appreciated in U.S. Pat. No. 4,484,822 to Hancock. Also in the prior art the process of dielectronomy is known where test samples are measured by their transmissiveness to microwaves under various conditions including heating.

SUMMARY OF THE INVENTION

It is an object of this invention to provide a device to determine melting point as it relates to pressure. It is important that pressure be considered when determining a melting point because at different pressures, a material at its melting point may have a variety of states.

It is a further object of this invention to provide a method where the viscosity/temperature relationship of semi-solids can be studied since the device of this invention includes means for recording any deformation of a sample at various pressures and at various temperatures. During the melting process, some materials change their absorption patterns in the spectrum and this invention incorporates means for measuring and recording such changes.

In its most basic form the device of this invention utilizes a powder made of the material that is to have its melting point determined. The powder is placed on a surface such as made from glassy carbon and heat is applied thereto within a chamber. The reflectance of light is measured within the chamber and when the powdered material which has a light color melts, it allows the black plate surface, such as of glassy carbon, black anodized material, black teflon or equivalent thereunder to show through, which plate when sensed changes the light reflectance level and a photocell measures such change in light intensity in the chamber. The temperature at which such change occurs indicates the melting point of the powdered material.

BRIEF DESCRIPTION OF THE PREFERRED EMBODIMENT(S)

Figure 1:
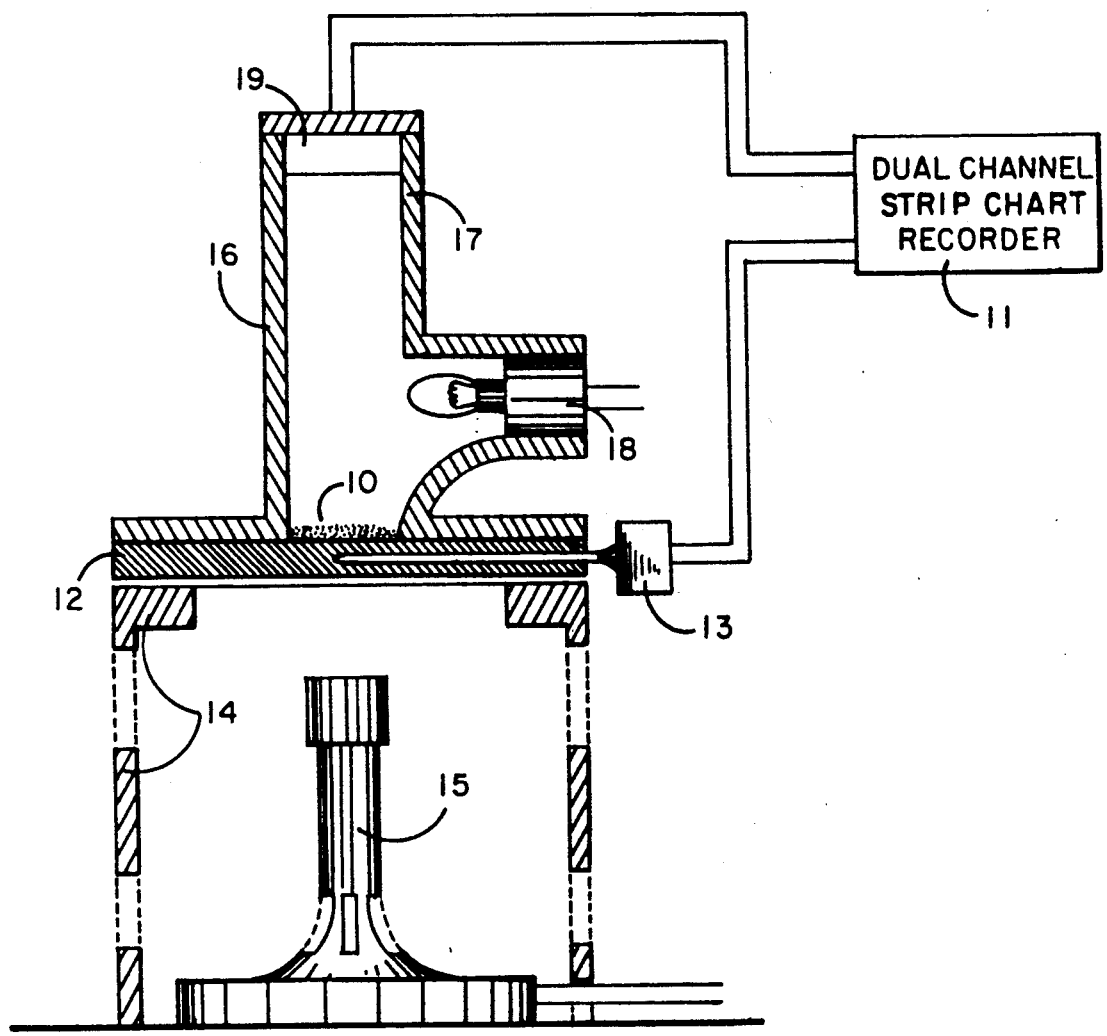
FIG. 1 illustrates a simplified version of the device of this invention.

FIG. 1 illustrates a basic embodiment of the device of this invention. A powder 10 of the sample material whose melting point is to be determined is dusted on the surface of plate 12. Plate 12 is a sample plate and can be made in some embodiments from glassy carbon which has the characteristics of natural blackness, high-temperature resistance, thermoconductivity and a very durable surface. Thermocouple 13 can be embedded in plate 12. The plate is supported on support member 14 above heat source 15. Collimator 16, which has mirror coating 17 on its inside surfaces and light source 18 embodied therein, is positioned over powder 10. At the top of the collimator is photocell 19 which is attached to a strip chart recorder which records the photocell's reactions to the light within collimator 16. The strip chart recorder also records the temperature of thermocouple 13 embedded in plate 12 over the same time period. The device of this invention relies on the change of reflectance within the collimator that occurs when sample powder 10 melts. It is well known that many substances take on a lighter color when they are ground to a fine powder. The lighter color or whiteness is due to an increased reflectivity of each of the particles within the ground powder. In practice powder 10 is placed on plate 12 and any excess is shaken off. In some cases a silicon oil can be rubbed on the plate's surface to provide some release of the melted powder to the plate. The collimator is then lowered onto the sample powder, and the heating is started. Light source 18 is turned on and photocell 19 relays to chart recorder 11 information regarding the constant light intensity which is the total reflectance within the collimator at the beginning of the process. Heat source 15 heats plate 12 to the melting point of the sample, when the particles that make up the powder fuse and clarify, which allows the light within the collimating chamber to be reflected directly down to the dark surface of sample plate 12 where the light, instead of being reflected, is absorbed. This absorbed portion of the total reflectance within the collimating chamber is no longer recorded by photocell 19 which will then sense a decrease in light intensity which lower intensity will be recorded on strip chart recorder 11. Since the temperature of the surface of plate 12 was also recorded at the same recording time, the comparison of the point of decrease of light within the chamber compared to the temperature at that time will yield the melting point of the substance being tested.

The sample can also be monitored by the device of this invention while cooling down and the reflectance in the collimating chamber measured when the sample turns opaque or otherwise changes in reflectivity such as when it might recrystallize.

Figure 2:
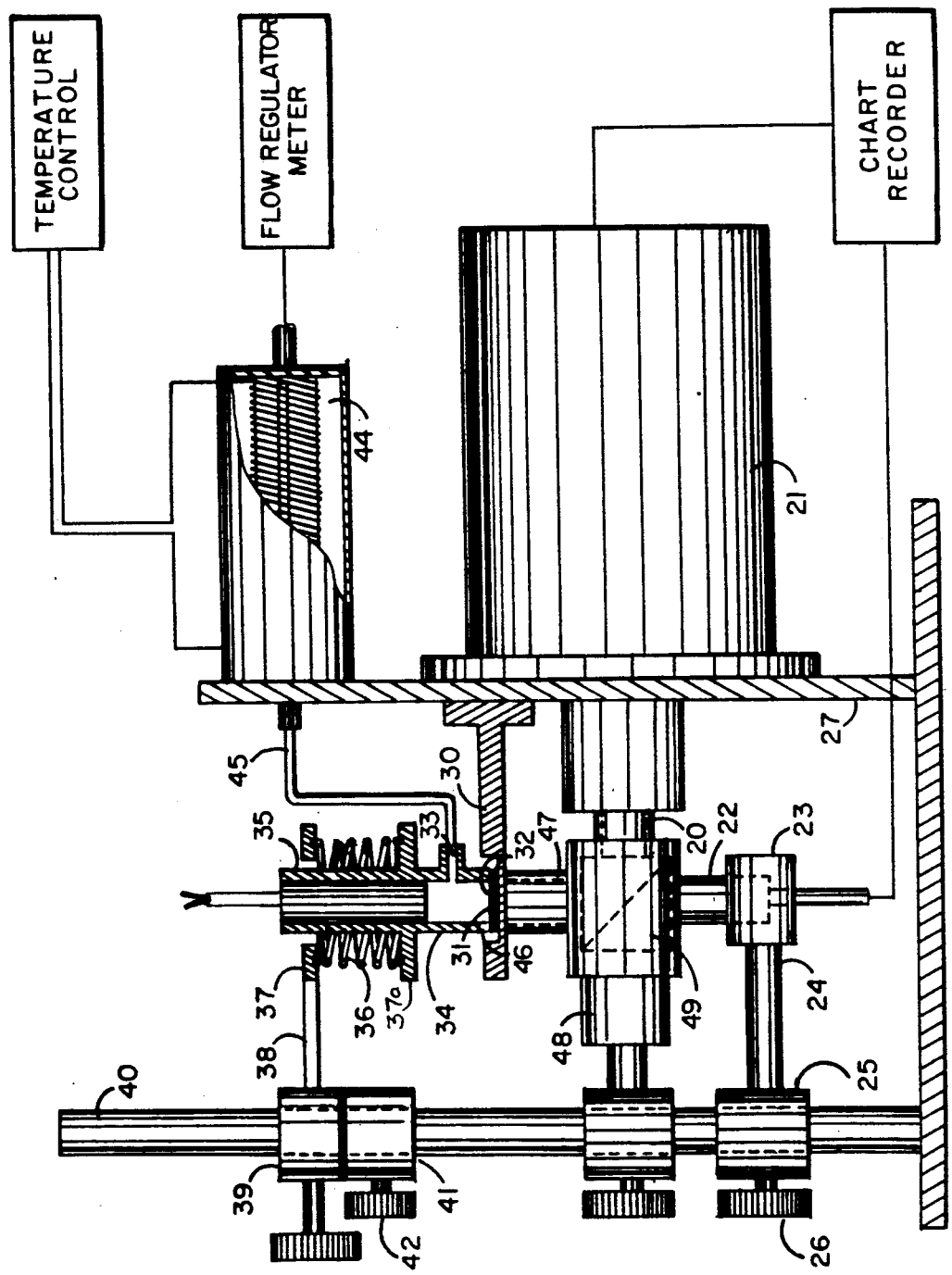
FIG. 2 illustrates an alternate embodiment of the device of this invention.

FIG. 2 illustrates a more complex embodiment of the device of this invention using similar principles. Sample 31 of the material to be tested is a powder which has been compressed into a wafer. This wafer is placed between two transparent disks 32 which could be made of glass or equivalent material which disks are supported on base 30. Collimator 34 is placed over the sample and also acts as a pressure transmitter. Light source 35 is located at the top of the collimator and heating gas can be entered directly into the collimator chamber through a tube from gas heating chamber 44. Pressure can be applied from the ends of the collimator pushing against upper transparent disk 32 through spring member 36 which urges the entire collimator downward a predetermined pressure measurement. Such pressure apparatus can include bar 38 which extends from upper spring catch member 37 which surrounds the collimator. Bar 38 is held by collar 39 on post 40. Stop member 41 can be held by thumb screw 42 at the desired height for the pressure to be applied on flange 37a on collimator 34 through spring member 36 with the height of spring catch member 37 dependent upon the amount of pressure one wishes to apply to the sample. Collimator 34 also has inlet 33 through which gas heated in chamber 44 is passed into the collimator through flexible tubing 45. After the gas impinges on the sample, it is vented through vent 46 at the bottom of the collimator. Below sample 31 is support housing 48 for beam splitter 49 which can be gold-silvered to divert thermal radiation from the sample through tube 20 to infrared scanner 21 which sends continuous temperature recordings to a recording chart recorder. The silvering in beam splitter 49 allows the light from light source 35 to pass also to photo detector 22 which is supported by element 23 which also can be held by bar 24 and slid on post 40 and held thereto by collar 25 by the tightening of thumb screw 26. When the wafer is first placed in the sample chamber, the beam from light source 35 is scattered internally within collimator 34 in many directions due to the particulate form of the sample as has been mentioned above with each particle defracting the light in a unique way thus imparting opacity or translucency to the sample. The temperature of the heating gas can be increased at a constant rate as desired so as to increase the temperature of the sample.

Due to the thickness of the wafer sample and the glass disks which have some thermal insulating qualities, one cannot always assume that the sample is at the identical temperature of the heating gas. Thus it is important to use an infrared scanner to read the temperature of the specimen through the beam splitter while at the same time measuring the change in light transmissivity by photodetector 22 at the bottom of the same beam splitter. When the temperature causes the material to fuse, the sample clarifies and flows, and the pressure from spring member 36 causes the sample wafer to be pressed thin between the disks. This simultaneous clarification and thinning causes the sample to transmit more light. As the temperature reading from the infrared scanner and the reading from the photodetector are recorded on a single dual chart strip recorder, the temperature at which the increase in light transmissivity occurred of the material being tested can be determined.

Figure 2A:
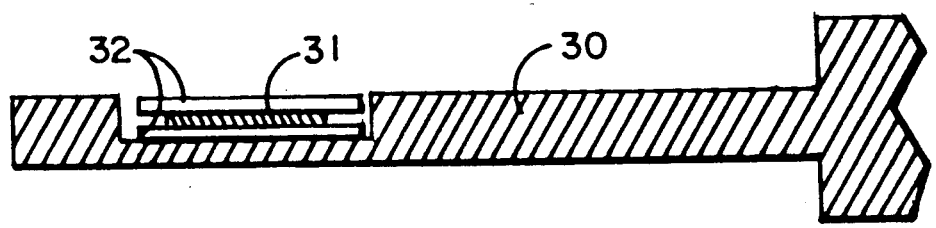
FIG. 2A illustrates the sample holding area of the device of FIG. 2 enlarged.

FIG. 2A is an enlarged view of sample 31 between transparent disks 32 supported on base 30.

To duplicate results, test samples must be weighed so that no more or no less of a sample is utilized in repetitive tests. Materials may have more than one reactive component that when such components chemically react, the melting point of the material changes.

Some materials that melt below room temperature, instead of being heated, can be cryogenically cooled such as with liquid nitrogen and then such cooling can be stopped and the material allowed to rise in temperature to the surrounding room during which rise in temperature the material's melting point will occur and be detected by the device of this invention.

Figure 3:
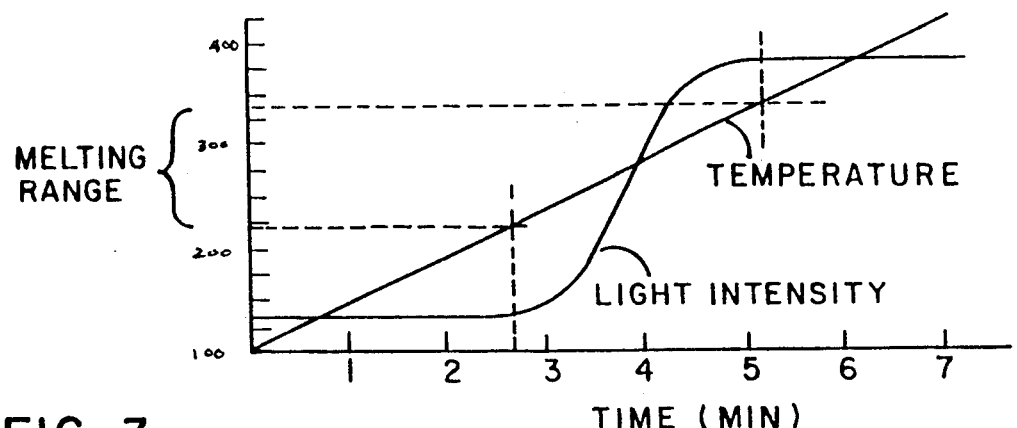
FIG. 3 illustrates a chart showing a typical curve of the recording of a melting point produced by the device of this invention.

FIG. 3 illustrates a typical chart recording produced by a device such as shown in FIG. 2. In this chart no pressure was used through spring member 36 so that any increase in light transmission was due solely to clarification. The rate of temperature increase is shown at 40 degrees F./minute. In this chart a change was seen in light transmissivity 2¾ minutes into the test which corresponded to 218 degrees F. on the melting range. The intensity of the light as seen by the photodetector steadily increased during the first 5 minutes of the test which increase corresponded to 325 degrees F. This is the melting range as indicated by the dotted lines. The substance then would have a total melting range between 218-325 degrees F.

Figure 4:
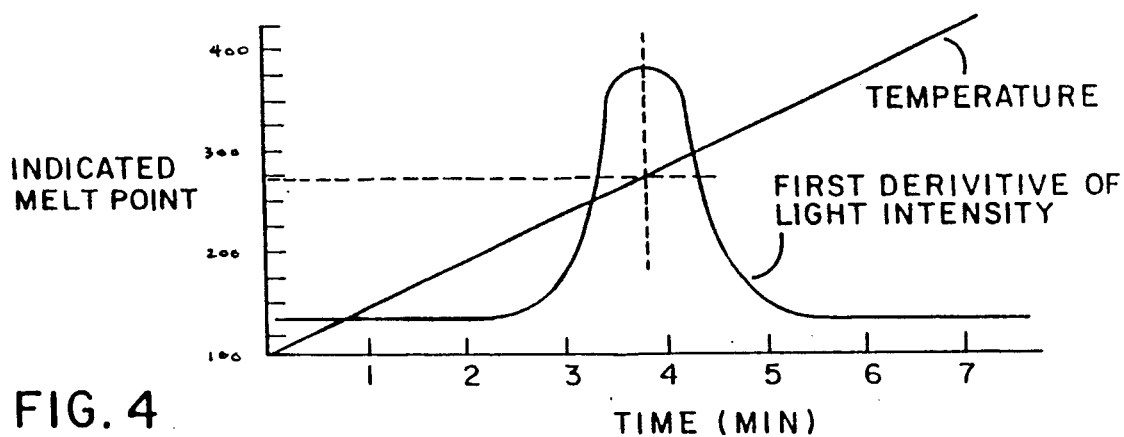
FIG. 4 illustrates a chart showing the rate of change of the melting of the material recorded in the chart of FIG. 3.

FIG. 4 illustrates the chart of FIG. 3 which is the reading of the output from the photodetector which is put through a first derivative computer that continuously calculates only the rate of change. The fastest rate of change is indicated by the lightest point on the bell-shaped curve which corresponds to 255 degrees F. degrees because this is the temperature at which the particles are fusing the fastest. Thus the 255 degrees F. mark could be designated as the melting point of the material.

Figure 5:
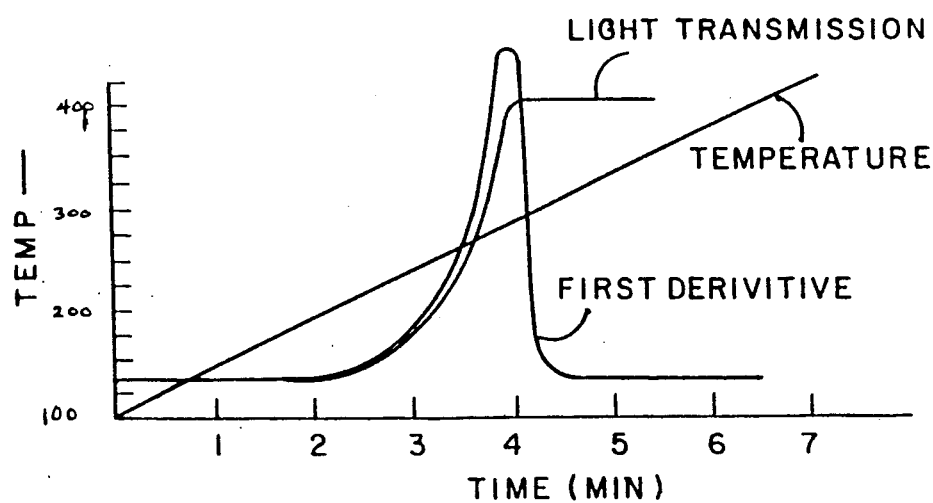
FIG. 5 illustrates a chart where a different pressure is applied to the same material being melted at the same rate of heating showing a shift in the start of the light transmission of the melting material.

FIG. 5 is a chart showing testing of the same substance using the same heating rate but applying a slight pressure from spring member 36. What is seen here is a shift to the left of the start of a change in light transmission. The point at which there is a change in light transmission indicates the material's softening point. The chart also shows that the rate at which the sample clarifies and thins increases with an increase in temperature. This chart visually describes the substance's change in viscosity versus temperature close to its melting point.

Figure 6:
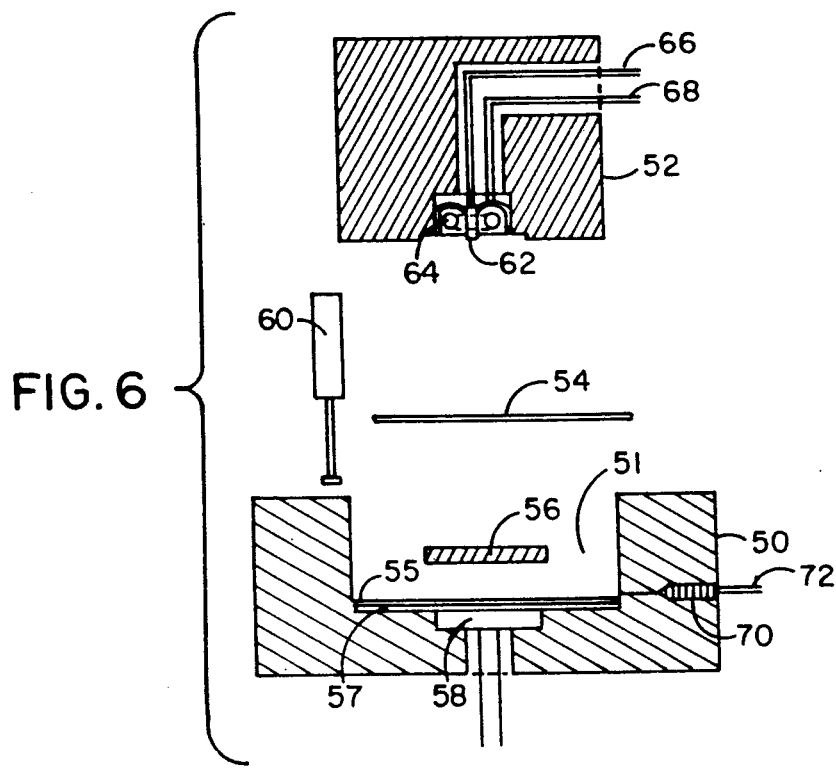
FIG. 6 illustrates a further alternate embodiment of the device of this invention.

A further embodiment of the device is disclosed in FIG. 6 which illustrates lower force member 50 having sample chamber 51 formed therein at the base of which is disposed an upwardly facing mirror 57 above heater unit 58 which can be an electric heater or equivalent. Disposed above mirror 57 is first transparent plate 55 which can be made of high-temperature resistant plastic film such as polyamid film, a plate of glass or equivalent material above which plate 55 is disposed sample material 56, which can be of the type having light reflective properties, to be tested. Sample material 56 is sandwiched by second transparent high-temperature resistant plate 54. In the top of sample chamber 51 is lowered an upper force member 52 which has centrally located within its bottom photocell 62 with power line 66 extending therefrom and around which is disposed toroidal lamp 64 with a power line 68 extending therefrom.

Figure 7:
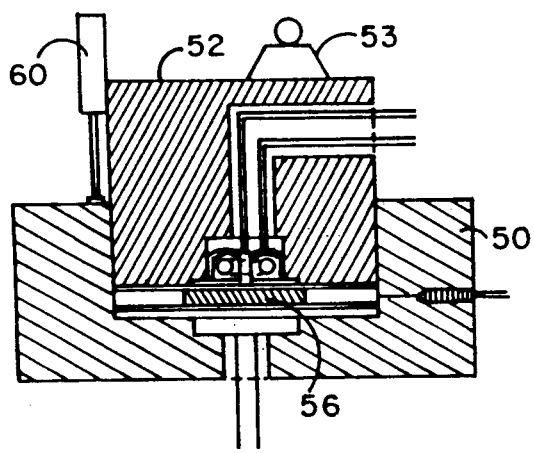
FIG. 7 illustrates the device of FIG. 6 with the force members engaged.
Figure 8:
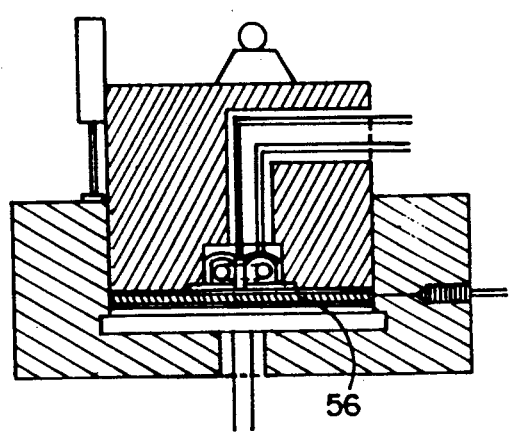
FIG. 8 illustrates the device of FIG. 6 with the sample material melted.

As seen in FIG. 7 upper force member 52 is placed within sample chamber 51 of lower force member 50, and a motion detector 60 measures the movement of upper force member 52 within sample chamber 51 of lower force member 50. A known weight or weights 53 can be placed on top of upper force member 52 as seen in FIGS. 7 and 8. A temperature thermocouple-type sensor 70 is disposed at the bottom of sample chamber 51 with electrical leads 72 extending therefrom. From the pressure on upper force member 52 as well as the increase in heat from heater 58, sample material 56 melts and spreads quickly between plates 54 and 55 as shown in FIG. 8. The toroidal light is then sensed by photocell 62 by reflection from mirror 57 when the sample has become translucent. In a similar manner to that of the above-described embodiments, chart recorders are attached to the electrical leads so that there can be a record and comparisons made of the linear motion, the temperature and the output of the photocell so that when the amount of reflected light changes when the sample material melts, the meltpoint can be determined when the sample clarifies. The outputs of motion detector 60, thermocouple type temperature sensor 70, and the output of photocell 62 can all be recorded together by a chart recorder for comparison as described above to determine the melting point of the sample being tested. As shown in FIG. 6, while temperature sensor 70 will only measure the material's edge temperature, it will still yield a true reading because by the time the material has reached the side of the sample chamber 51, the center of the chamber above heater 58 may be hotter than the melting point. The material flows when melted and cools with higher viscosity at the edges than at the center of sample chamber 51. Different temperature ramps or rates of temperature increase can be used. A slow temperature ramp may cause a material to degrade which degradation is important to measure. By using varied temperature ramps, information on material degradation due to long-term heating can be obtained. Slow temperature ramp determinations can show how the material's melting point temperature can be affected by its heat history. In some cases it is desirable to have repeated tests with multiple runs under different conditions of weight and different temperature ramps to best determine the melting point of a material.

Although the present invention has been described with reference to particular embodiments, it will be apparent to those skilled in the art that variations and modifications can be substituted therefor without departing from the principles and spirit of the invention.

I claim:

1. A device for determining the melting point of a powdered material having light-reflective properties, comprising:
   a low-reflectance plate having a lower reflectance than the reflectance of said powdered material, said plate having said powdered material positioned thereon;
   a chamber having an inside surface, said chamber being placed over said powdered material;
   a reflective coating on said chamber's inside surface;
   a light source positioned in said chamber to produce light in said chamber;
   a photodetector positioned in said chamber, said photodetector to measure the total light intensity in said chamber;
   a heat-measuring device adapted to measure the heat on said plate;
   a recording device adapted to record the light intensity measured by said photodetector in said chamber and the heat measured by said heat measuring device; and
   a heat source adapted to heat said plate, said device operative by increasing the temperature on said plate by said heat source to melt said powdered material thereby causing it to change in light reflectivity, said changed amount of light reflection lowering the total light intensity in said chamber recorded by said recording device at the temperature of the melting point of the powdered material.

2. A material melting point determination apparatus having the material whose melting point is to be determined in a powdered state, said apparatus comprising:
   two optically transparent carrier disks sandwiching said powdered material therebetween;
   a chamber positioned over said transparent disks with said powdered material therebetween;
   a light source within said chamber shining on said powdered material;
   means to apply pressure to the top of said topmost disk;
   means to enter heated gas into said chamber to be directed against said disks to heat and melt to a fluid state said powdered material therebetween, said transparent disks compressing said melted powdered material when in its fluid state to simultaneously thin, spread and clarify said melted powder;
   vent means in said chamber to allow the escape of heated gas;
   means to determine the temperature of said material;
   means to determine the optical transmissivity from the light source within said chamber through said material as said material is being heated to its melting point; and
   recording means to receive the temperature reading when said optical transmissivity means indicate said material has melted at its point of translucency.

3. The apparatus of claim 2 further including a beam splitter directing a portion of the light passing through said material to an infrared temperature measuring device which transmits its temperature reading to a chart recorder with the other portion of the beam being split directed to a photo-optical detector to measure the light intensity of the light passing through said material with such light intensity also being recorded on said chart recorder.

4. A method for determining the melting point of a material having light-reflective properties comprising the steps of:

powdering said material;
  positioning said powdered material on a plate having a lower reflectance than the reflectance of said powdered material;
  enclosing said plate in a chamber;
  illuminating said chamber;
  detecting the light level in said chamber;
  recording the light level in said chamber;
  heating said plate to melt said material;
  making said material translucent by said melting;
  changing the level of light reflecting in said chamber by exposing said low reflectance plate through said translucent material; and
  measuring the temperature of said plate at the point of changed light reflectancy in said chamber.

5. A device for determining the melting point of a sample material having light reflective properties, comprising:

a lower force member having a chamber defined therein;
  heating means disposed at the base of said chamber in said lower force member;
  a mirror disposed at the base of said chamber above said heating means;
  a first transparent plate disposed above said mirror;
  a second transparent plate adapted to be positioned above said first plate with said sample material disposed therebetween;
  an upper force member of a size able to be positioned within said chamber in said lower force member;
  a photocell disposed at the bottom of said upper force member;
  light means disposed at the bottom of said upper force member;
  means to move said upper force member into said chamber in said lower force member and to move said second clear plate to apply pressure to said sample material while said heating means increases the temperature within said chamber in said lower force member to melt said sample material, said means for moving said upper force member into said chamber of said lower force member adapted to apply pressure on said sample material when melted to fill the area between said second transparent plate and said first transparent plate as said sample material is melted;
  means to measure the amount of movement of said upper force member into said lower force member;
  means to sense the temperature within said chamber within said lower force member while said sample material is in the process of being melted and spread within the area between said second transparent plate and said first transparent plate as said movement means moves said upper force member within said chamber; and
  means to compare the amount of light detected by said photocell to the temperature within said chamber when said sample light transmissivity changes as said sample material is melted under pressure in said chamber.

* * * * *